(12) United States Patent
Iharada

(10) Patent No.: US 9,360,466 B2
(45) Date of Patent: Jun. 7, 2016

(54) SAMPLE INTRODUCTION MECHANISM FOR TOTAL ORGANIC CARBON METER

(71) Applicant: SHIMADZU CORPORATION, Kyoto-shi, Kyoto (JP)

(72) Inventor: Takeshi Iharada, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 7 days.

(21) Appl. No.: 14/326,704

(22) Filed: Jul. 9, 2014

(65) Prior Publication Data

US 2016/0011165 A1    Jan. 14, 2016

(51) Int. Cl.
*G01N 33/18* (2006.01)
*G01N 30/88* (2006.01)
*G01N 33/00* (2006.01)

(52) U.S. Cl.
CPC ........ *G01N 33/1846* (2013.01); *G01N 33/0004* (2013.01); *G01N 2030/884* (2013.01)

(58) Field of Classification Search
CPC ................................................. G01N 33/1846
USPC ...................................... 422/78–80
See application file for complete search history.

(56) References Cited

U.S. PATENT DOCUMENTS

2010/0159602 A1*  6/2010  Conway ............. G01N 33/1846
                                                                  436/43

FOREIGN PATENT DOCUMENTS

| JP | 05-052837 A | | 3/1993 |
| JP | 06249843 A | * | 9/1994 |
| JP | 2013170934 A | * | 9/2013 |

OTHER PUBLICATIONS

English Machine Translation, JP2013170934 A, No Date.*
English Machine Translation, JP 06249843 A, No Date.*

* cited by examiner

*Primary Examiner* — Jill Warden
*Assistant Examiner* — Julie Tavares
(74) *Attorney, Agent, or Firm* — Sughrue Mion, PLLC

(57) ABSTRACT

A total organic carbon meter including a sample introduction mechanism that includes a case in which a sample introduction and rod opening is formed; a sample introduction rod at the front end part of which a sample tray is arranged and which is inserted in the set direction through the sample introduction and rod opening; and a cover formed on the outer circumferential surface of the sample introduction rod, wherein the insertion of the sample introduction rod, on the front end part of which a sample tray has been arranged, through the sample introduction and rod opening, causes the gap between the sample introduction and rod opening and the sample introduction rod to be closed by the cover.

2 Claims, 3 Drawing Sheets

SAMPLE INTRODUCTION MECHANISM FOR TOTAL ORGANIC CARBON METER

TECHNICAL FIELD

The present invention relates to a total organic carbon meter which measures carbon content in samples including solid samples such as soil, sediment and agricultural and livestock products and liquid samples such as river water, lake and marsh water, sea water, rain water and ground water.

BACKGROUND ART

In recent years, measurement of organic carbon concentration in municipal water and wastewater, water for various sorts of plants, river water and the like, has become an important item of pollution surveys and the like. Total organic carbon meters (TOC meters) are used for such measurement of organic carbon concentration.

Moreover, the demand for TOC measurement has expanded to solid samples. In TOC meters for measurement of solid samples, a set quantity of solid sample is placed onto a ceramic sample tray and each sample tray is inserted into a quartz glass combustion tube, whereby the organic matter in the solid sample is combusted (subjected to an oxidation reaction), and the generated carbon dioxide is measured with an infrared detector.

Figure 5:
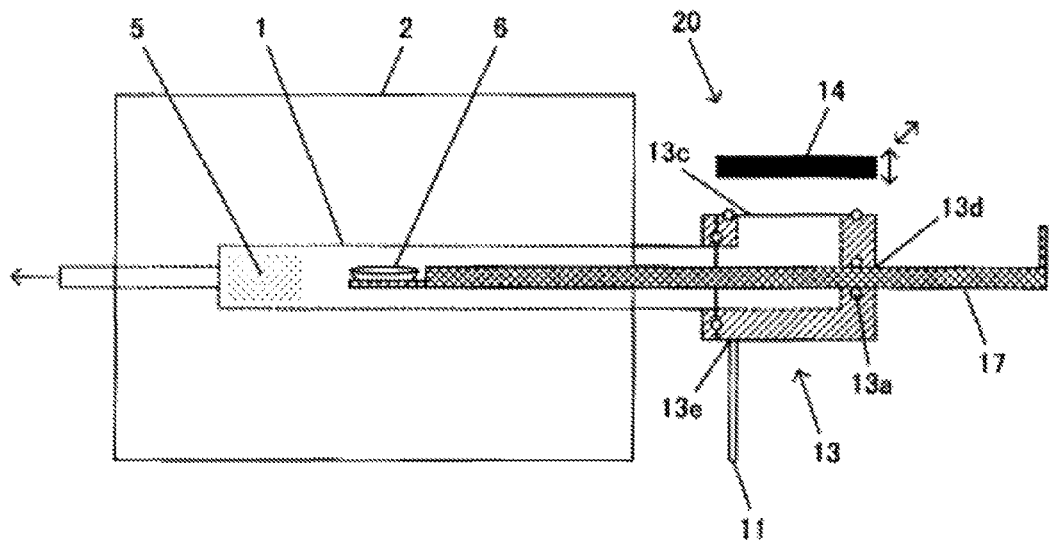
Figure 6:
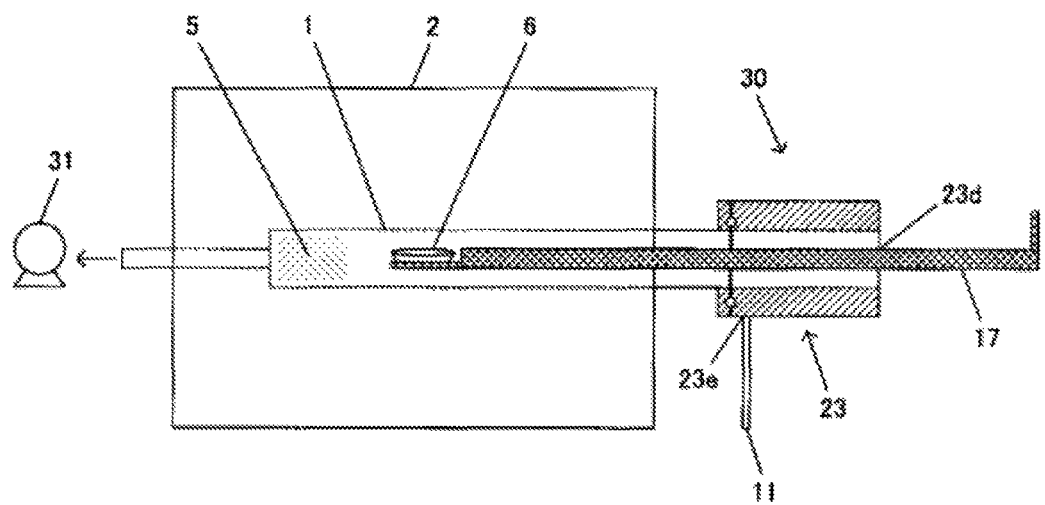

In this sort of TOC meter, combustion tube 1 is arranged horizontally inside a tubular combustion reaction furnace (combustion furnace) 2 heated to about 900° C. so that the sample tray 6 inserted into the combustion tube 1 will be heated (see FIG. 5 and FIG. 6). Furthermore, a carrier gas inlet 11 is formed at one end part (the right part) of the combustion tube 1 so that carrier gas (for example, oxygen gas of 99.99 weight percent purity) will flow through the inside of the combustion tube 1 in a fixed direction (for example, from right to left). Furthermore, the other end part (left part) of the combustion tube 1 is filled with an oxidation catalyst 5, the carbon content, etc. generated from the solid sample reaches the oxidation catalyst layer 5 together with the carrier gas, and is oxidized by the oxidation catalyst, turning into carbon dioxide.

To the other end part (left part) of the combustion tube 1, a non-dispersive infrared sensor (NDIR) is connected across a drain separator, and the carbon dioxide gas and carrier gas from the combustion tube 1 are guided to the NDIR, and the carbon content in the solid sample is detected (for example, see Patent Literature 1).

Using this sort of TOC meter, in order for the operator to replace a sample tray 6 on which one solid sample has been placed with a sample tray 6 on which the next solid sample has been placed, the temperature of the replacement work area has to be kept low, so one end part (the right part) of the combustion tube 1 is formed so as to protrude a certain distance outside the electric furnace 2, and a sample introduction port section (sample introduction mechanism) is connected to that one end part (right part) of the combustion tube 1. Furthermore, the operator pushes the sample tray 6 arranged inside one end part of the combustion tube 1 with a sample introduction rod 17 through the sample introduction port section, thereby moving it in a set direction (for example, from right to left) and arranging it inside the central part of the combustion tube 1.

Here, FIG. 5 is a simplified diagram of one example of the sample introduction port section of a conventional TOC meter.

Sample introduction port section 20 comprises a round tubular case 13 with a sample introduction opening 13c formed in the top wall, a round (for example, 6 mm diameter) rod opening 13d formed in the right wall and a gas introduction opening 13e formed in the bottom wall, a cover 14 arranged on the sample introduction opening 13c, a sample introduction rod 17 inserted across an O-ring 13a in a set direction through the rod opening 13d, and a carrier gas inlet 11 connected to gas inlet opening 13e.

Sample introduction rod 17 is made of stainless steel and has a 6 mm diameter cylindrical shape, made so that a sample tray 6 can be arranged on its front end part and having a manipulation handle formed on its rear end part.

Cover 14 is designed to move several mm up and down through turning of a screw, and is designed to ensure airtightness of the inside of the case 13 by tightly fitting to the periphery of the sample introduction opening 13c in the top wall when positioned in its lower position and to allow opening of the inside of the case 13 by sliding horizontally when in its upper position.

Furthermore, when analyzing a solid sample arranged inside the central part of the combustion tube 1, carrier gas is introduced at 500 ml/min into the case 13 through the carrier gas inlet 11, and the carrier gas flows through the inside of the combustion tube 1 in a set direction (for example, from right to left) at 500 ml/min.

With this sort of sample introduction port section 20, the operator positions the cover 14 at the upper position by turning the handle at the top end of the screw with his hand, slides the cover 14 with his hand horizontally, and then arranges a sample tray 6 at the front end part of the sample introduction rod 17 located inside the case 13 through the sample introduction opening 13c. The operator then slides the cover 14 horizontally with his hand and turns the handle at the top end of the screw with his hand, thereby positioning the cover 14 at the lower position. Next, the operator moves the sample introduction rod 17 by pushing it in the set direction, thereby arranging the sample tray 6 in the central part of the inside of the combustion tube 1.

Furthermore, FIG. 6 is a simplified diagram of another example of the sample introduction port section of a conventional TOC meter. Parts which are the same as in the sample introduction port section 20 described above will be assigned the same reference symbols.

Sample introduction port section 30 comprises a round tubular (for example, 30 mm diameter) sample introduction and rod opening 23d in the right wall, a round tubular case 23 with a gas introduction opening 23e formed in its bottom wall, a sample introduction rod 17 which is inserted in a set direction through the sample introduction and rod opening 23d, and a carrier gas inlet 11 connected to the gas introduction opening 23e.

A fixed flow rate pump 31 which suctions 500 ml/min is connected to the other end part (left part) of the combustion tube 1.

To analyze a solid sample arranged inside the central part of the combustion tube 1, carrier gas is introduced at 1,000 ml/min into the case 23 through carrier gas inlet 11, carrier gas is made to flow through the inside of the combustion tube 1 in a set direction (for example, from right to left) by the fixed flow rate pump 31 at 500 ml/min, and the quantity of carrier gas exceeding the flow rate suctioned by fixed flow rate pump 31 is discharged through the gap between the sample introduction and rod opening 23d and sample introduction rod 17. This prevents air from entering inside the combustion tube 1.

With this sort of sample introduction port section 30, the operator arranges a sample tray 6 at the front end part of the sample introduction rod 17, and then inserts the sample introduction rod 17 with his hand inside the case 23 through the sample introduction and rod opening 23d. Next, the operator moves the sample introduction rod 17 by pushing it with his hand in the set direction, thereby arranging the sample tray 6 in the central part inside the combustion tube 1.

PRIOR ART LITERATURES

Patent Literatures (Patent literature 1) Japanese Unexamined Patent Application Publication H5-52837

However, with a sample introduction port section 20 as described above, there is the problem that a cover structure in which a sample introduction opening 13c for arranging a sample tray 6 is manually opened and closed is necessary, and the operating procedure for arranging the sample tray 6 inside the case 13 becomes longer.

Furthermore, with a sample introduction port section 30 as described above, there is the problem that a fixed flow rate pump 31 is necessary in order to make carrier gas flow at 500 ml/min in a set direction through the inside of the combustion tube 1, and a large amount of carrier gas is wasted.

Thus, it is an object of the present invention to provide a total organic carbon meter capable of closing the opening upon placement of a sample.

SUMMARY OF THE INVENTION

The total organic carbon meter of the present invention, made to resolve the problems described above, is a total organic carbon meter wherein a sample tray on which a sample has been placed is arranged inside a sample introduction mechanism connected to one end of a combustion tube and is then moved by a sample introduction rod in a set direction from one end of said combustion tube toward the other end, and is thereby arranged inside the central part of said combustion tube which is inside a combustion furnace, and organic material inside said sample combusts, wherein said sample introduction mechanism comprises: a case in which a sample introduction and rod opening is formed; a sample introduction rod at the front end part of which a sample tray is arranged and which is inserted in said set direction through the sample introduction and rod opening; and a cover formed on the outer circumferential surface of said sample introduction rod, wherein the insertion of the sample introduction rod, on the front end part of which a sample tray has been arranged, through the sample introduction and rod opening, causes the gap between said sample introduction and rod opening and said sample introduction rod to be closed by the cover.

With the total organic carbon meter of the present invention, as described above, there is no need for a fixed flow rate pump or a cover structure in which the opening is opened and closed manually. Furthermore, the waste of carrier gas is reduced. Moreover, the operating procedure for arranging the sample tray inside the case is simpler.

Furthermore, the invention described above may be made such that said cover is formed so as to be movable in the direction opposite to the set direction over the outer circumferential surface of said sample introduction rod, and the gap between said sample introduction and rod opening and said sample introduction rod is closed by the cover when the sample introduction rod with a sample tray placed on its front end part is inserted through the sample introduction and rod opening so as to arrange the sample tray inside one end of said combustion tube, and, with the gap between said sample introduction and rod opening and said sample introduction rod being closed by the cover, said sample introduction rod is inserted in the set direction, causing said sample tray to be arranged inside the central part of the combustion tube.

Moreover, in the invention described above, an elastic member which acts so as to make said cover move in the set direction in relation to said sample introduction rod may be mounted on said sample introduction rod.

BRIEF DESCRIPTION OF THE DRAWINGS (FIG. 1) A simplified diagram of an example of the sample introduction rod of a TOC meter according to the present invention.

(FIG. 2) A simplified diagram of an example of the sample introduction port section of a TOC meter according to the present invention.

(FIG. 3) A simplified diagram of an example of the sample introduction port section of a TOC meter according to the present invention.

(FIG. 4) A simplified diagram of an example of the sample introduction port section of a TOC meter according to the present invention.

(FIG. 5) A simplified diagram of an example of the sample introduction port section of a conventional TOC meter.

(FIG. 6) A simplified diagram of another example of the sample introduction port section of a conventional TOC meter.

DETAILED DESCRIPTION OF THE EXEMPLARY EMBODIMENTS

Modes of embodiment of the present invention will be described below using the drawings. It should be noted that the present invention is not limited to the modes of embodiment described below and includes various modes which do not depart from the gist of the present invention.

Figure 1:
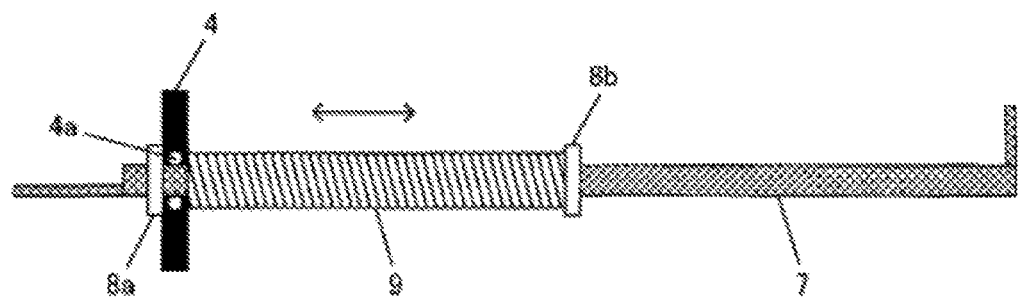
Figure 2:
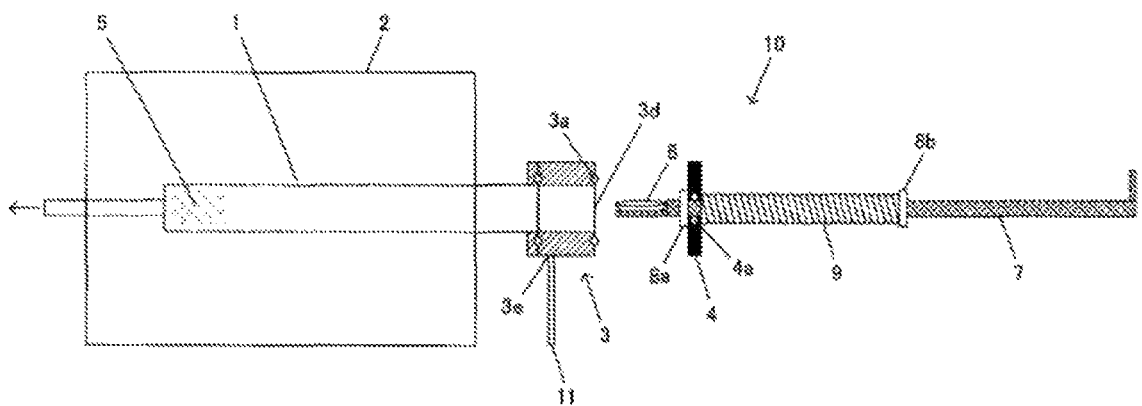
Figure 3:
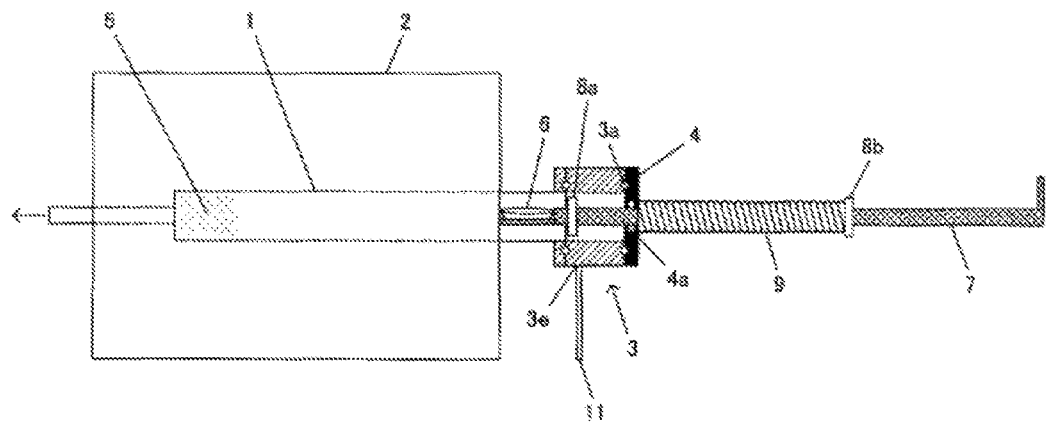
Figure 4:
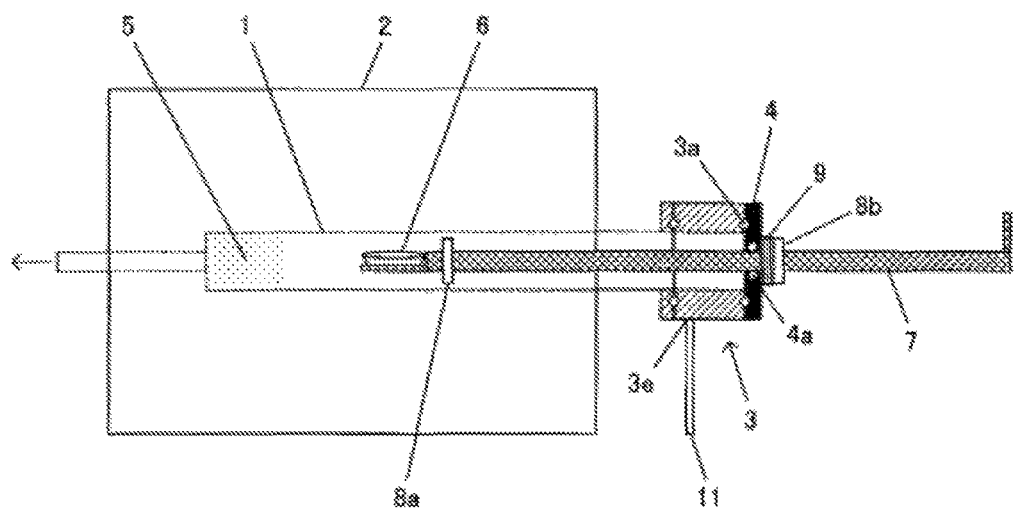

FIG. 1 is a simplified diagram of an example of the sample introduction rod of a TOC meter according to the present invention, and FIG. 2 through FIG. 4 are simplified diagrams of examples of the sample introduction port section of a TOC meter according to the present invention. Parts which are the same as in the sample introduction port section 30 described above will be assigned the same reference symbols.

Sample introduction port section 10 comprises a round tubular case 3 with a round (for example, 20 mm diameter) sample introduction and rod opening 3d formed in its right wall and a gas introduction opening 3e formed in its bottom wall; a sample introduction rod 7 which is inserted in a set direction through the sample introduction and rod opening 3d; and a carrier gas inlet 11 connected to the gas introduction opening 3e.

Sample introduction rod 7 is made of stainless steel and has a 6 mm diameter cylindrical shape, and is designed to have a sample tray 6 placed on its front end part and has a manipulation handle formed on its rear end part.

The cover 4 is made of stainless steel and has an annular shape with a thickness of 5 mm and a diameter of 40 mm, and the sample introduction rod 7 is inserted across an O-ring 4a through the annular opening (for example, 6 mm in diameter) thereof. As a result, the cover 4 allows movement in the set direction while maintaining air-tightness. Furthermore, a stainless steel stopper 8a which protrudes perpendicularly to the set direction and a stainless steel stopper 8b which protrudes perpendicularly to the set direction are formed on the sample introduction rod 7. Stopper 8a is formed near the front end part, and stopper 8*b* is formed near the central part. Furthermore, the cover 4 is arranged between the stopper 8*a* and stopper 8*b*.

A spring (elastic member) 9 which acts so as to make the cover 4 move in the set direction is mounted between the cover 4 and the stopper 8*b*. As a result, the cover 4 is moved by the spring 9 in the set direction in relation to the sample introduction rod 7 and is thereby pushed against the stopper 8*a*.

When a solid sample which has been arranged inside the central part of the combustion tube 1 is to be analyzed, carrier gas is guided at 500 ml/min inside the case 3 through the carrier gas inlet 11, so that carrier gas flows through the inside of the combustion tube 1 at 500 ml/min in the set direction (from right to left) at 500 ml/min.

Here, an example will be described of the method by which the operator using the TOC meter replaces a sample tray 6 on which one solid sample has been placed with a sample tray 6 on which the next solid sample has been placed.

First, the operator arranges a sample tray 6 at the front end part of the sample introduction rod 7 (see FIG. 2). Next, the operator manually inserts the sample introduction rod 7 into the case 3 through the sample introduction and rod opening 3*d* (see FIG. 3). Here, when the sample tray 6 comes to be arranged inside one end part of the combustion tube 1, the cover 4 fits tightly across the O-ring 3*a* against the circumferential portion of the sample introduction and rod opening 3*d* of the case 3, whereby the gap between the sample introduction and rod opening 3*d* and the sample introduction rod 7 is closed by the cover 4. Furthermore, in order to push out air which has infiltrated in the state of FIG. 2 by introducing carrier gas at 500 ml/min inside the case 3 through the carrier gas inlet 11, the carrier gas is purged for a set period of time (for example, 60 seconds). At this time, the operator may continue holding the sample introduction rod 7 with his hand or secure it with something.

Next, with the gap between the sample introduction and rod opening 3*d* and sample introduction rod 7 being closed by the cover 4, the operator moves the sample tray 6 by pushing the sample introduction rod 7 in the set direction with his hand and arranges it inside the central part of the combustion tube 1 (see FIG. 4). Here, carrier gas is introduced at 500 ml/min into the case 3 through carrier gas inlet 11, causing carrier gas to flow in the set direction (for example, from right to left) through the inside of the combustion tube 1 at 500 ml/min. Furthermore, the other end part (left part) of the combustion tube 1 is filled with an oxidation catalyst 5, organic matter, etc. generated from the solid sample reaches the oxidation catalyst layer 5 together with the carrier gas, and is oxidized by the oxidation catalyst 5 to form carbon dioxide. At this time, the operator may continue holding the sample introduction rod 7 with his hand or may secure it with something.

Furthermore, when analysis of the solid sample has been completed, the operator pulls the sample introduction rod 7 with his hand from the sample introduction and rod opening 3*d* in the direction opposite to the set direction (see FIG. 3). Moreover, the operator, by pulling the sample introduction rod 7 in the direction opposite to the set direction with his hand, removes the sample introduction rod 7 from the sample introduction and rod opening 3*d* (see FIG. 2). Furthermore, the operator performs replacement of the sample tray 6 on which one solid sample has been placed with a sample tray 6 on which the next solid sample has been placed.

With the sample introduction port section 10 of the present invention, as described above, a fixed flow rate pump and a cover structure wherein a sample introduction opening is opened and closed manually becomes unnecessary. Furthermore, waste of carrier gas is also eliminated. Moreover, the operating procedure for arranging the sample tray 6 inside the case 3 becomes simpler.

OTHER MODES OF EMBODIMENT (1) In the TOC meter described above, a configuration was presented wherein the operator pushes the sample introduction rod 7 in by hand, but a configuration in which the sample introduction rod 7 is pushed in by a motor or solenoid is also possible.

(2) In the TOC meter described above, a configuration was presented wherein the cover 4 was kept tight against the circumferential part of the sample introduction and rod opening 3*d* of the case 3 by means of a spring 9, but a configuration in which the cover 4 is kept tight against the circumferential part of the sample introduction and rod opening 3*d* of the case 3 by means of a motor or solenoid is also possible.

INDUSTRIAL APPLICABILITY

The present invention can be applied to total organic carbon meters which measure the carbon content in samples including solid samples such as soil, sediment and agricultural and livestock products and liquid samples such as river water, lake and marsh water, sea water, rain water and ground water, and the like.

DESCRIPTION OF REFERENCES

1 Combustion tube
2 Electric furnace (combustion furnace)
3 Case
4 Cover
3*d* Sample introduction and rod opening
6 Sample tray
7 Sample introduction rod
10 Sample introduction port section (sample introduction mechanism)

What is claimed is:

1. A sample introduction mechanism configured to be used with a total organic carbon meter, the sample introduction mechanism comprising:
   a sample introduction rod comprising a sample tray for placing a sample thereon arranged at a front end part of the sample introduction rod;
   a case configured to be connected to one end of a combustion tube of a combustion furnace, wherein a sample introduction rod opening is formed in the case;
      wherein the sample introduction rod is configured to be inserted through the sample introduction rod opening such that the sample tray is moved by the sample introduction rod in a set direction from one end of the combustion tube toward another end, and the sample tray is thereby arranged inside a central part of the combustion tube whereby organic material inside the sample combusts;
   a cover formed on an outer circumferential surface of the sample introduction rod; and
   an elastic member mounted on the sample introduction rod which urges the cover to move in the set direction in relation to the sample introduction rod;
      wherein the elastic member is coupled to the sample introduction rod such that insertion of the sample introduction rod through the sample introduction rod opening causes a gap between the sample introduction rod opening and said sample introduction rod to be closed by the cover.

2. The sample introduction mechanism of claim 1, wherein said cover is formed so as to be movable in the direction opposite to the set direction over the outer circumferential surface of said sample introduction rod, and the gap between said sample introduction and rod opening and said sample introduction rod is closed by the cover when the sample introduction rod with the sample tray placed on its front end part is inserted through the sample introduction rod opening so as to arrange the sample tray inside one end of said combustion tube, and with the gap between said sample introduction and rod opening and said sample introduction rod being closed by the cover, said sample introduction rod is inserted in the set direction, causing said sample tray to be arranged inside the central part of the combustion tube.

* * * * *